(12) United States Patent
Buri et al.

(10) Patent No.: US 10,836,646 B2
(45) Date of Patent: Nov. 17, 2020

(54) DRY PROCESS FOR PREPARING A SURFACE-MODIFIED ALKALINE EARTH METAL CARBONATE-CONTAINING MATERIAL

(71) Applicant: Omya International AG, Oftringen (CH)

(72) Inventors: Matthias Buri, Rothrist (CH); Samuel Rentsch, Spiegel bei Bern (CH); Patrick A. C. Gane, Rothrist (CH); René Vinzenz Blum, St. Urban (CH)

(73) Assignee: Omya International AG, Blue Ash, OH (US)

( * ) Notice: Subject to any disclaimer, the term of this patent is extended or adjusted under 35 U.S.C. 154(b) by 748 days.

(21) Appl. No.: 15/510,771

(22) PCT Filed: Sep. 3, 2015

(86) PCT No.: PCT/EP2015/070162
§ 371 (c)(1),
(2) Date: Mar. 13, 2017

(87) PCT Pub. No.: WO2016/041781
PCT Pub. Date: Mar. 24, 2016

(65) Prior Publication Data
US 2017/0275175 A1   Sep. 28, 2017

(30) Foreign Application Priority Data

Sep. 15, 2014  (EP) ..................... 14184762

(51) Int. Cl.
*C09C 1/02* (2006.01)
*C01F 11/18* (2006.01)
*C08K 3/22* (2006.01)
*C08K 3/26* (2006.01)
*A61K 8/19* (2006.01)
*D21H 19/38* (2006.01)
*A61K 8/55* (2006.01)
*A61K 8/02* (2006.01)
*A61Q 19/00* (2006.01)
*C08K 9/04* (2006.01)

(52) U.S. Cl.
CPC .......... *C01F 11/185* (2013.01); *A61K 8/0241* (2013.01); *A61K 8/19* (2013.01); *A61K 8/55* (2013.01); *A61Q 19/00* (2013.01); *C08K 3/22* (2013.01); *C08K 3/26* (2013.01); *C08K 9/04* (2013.01); *C09C 1/021* (2013.01); *D21H 19/385* (2013.01); *A61K 2800/10* (2013.01); *A61K 2800/612* (2013.01); *A61K 2800/651* (2013.01); *C08K 2003/262* (2013.01); *C08K 2201/005* (2013.01); *C08K 2201/006* (2013.01)

(58) Field of Classification Search
CPC .......... C01F 11/185; C08K 3/26; C08K 9/04; C08K 2003/262; C09C 1/021; D21H 19/385
See application file for complete search history.

(56) References Cited

U.S. PATENT DOCUMENTS

| 4,186,028 | A | 1/1980 | Woditsch et al. |
|---|---|---|---|
| 4,802,990 | A | 2/1989 | Inskeep, Jr. |
| 5,145,902 | A | 9/1992 | Ravet et al. |
| 8,440,298 | B2 | 5/2013 | Gane et al. |
| 2005/0096233 | A1 | 5/2005 | Hurtevent et al. |
| 2012/0077917 | A1 | 2/2012 | Gane et al. |
| 2013/0116372 | A1 | 5/2013 | Hucaluk et al. |
| 2013/0190441 | A1 | 7/2013 | Vucak et al. |
| 2013/0197142 | A1* | 8/2013 | Buri ............... C08K 13/02 524/354 |
| 2014/0024761 | A1 | 1/2014 | Kasahara et al. |
| 2015/0040800 | A1 | 2/2015 | Gane et al. |

FOREIGN PATENT DOCUMENTS

| DE | 4404219 A1 | 8/1995 | |
|---|---|---|---|
| EP | 1151966 A1 | 11/2001 | |
| EP | 2194103 A1 | 6/2010 | |
| EP | 2644568 A1 | 10/2010 | |
| EP | 2377900 A1 | 10/2011 | |
| EP | 2 644 568 | * 10/2013 | ............... C09C 1/02 |
| FR | 2393037 | 12/1978 | |
| FR | 2765495 A1 | 1/1999 | |
| JP | S57168954 A | 10/1982 | |
| JP | H07331038 A | 12/1995 | |
| JP | 2005042128 A | 2/2005 | |
| TW | 201338842 A | 10/2013 | |
| WO | 2002089991 A2 | 11/2002 | |
| WO | 2007138410 A1 | 12/2007 | |
| WO | WO-2012141236 A1 | 10/2012 | |

OTHER PUBLICATIONS

International Search Report dated Nov. 17, 2015 for PCT/EP2015/070162.
The Written Opinion of the International Searching Authority dated Nov. 17, 2015 for PCT/EP2015/070162.

* cited by examiner

*Primary Examiner* — Pegah Parvini
(74) *Attorney, Agent, or Firm* — Schwegman Lundberg & Woessner, P.A.

(57) ABSTRACT

The present invention relates to a process to modify at least part of the surface of an earth alkaline metal carbonate-containing material in a dry blending process as well as to a mineral product obtainable by the inventive process and uses thereof.

15 Claims, No Drawings

DRY PROCESS FOR PREPARING A SURFACE-MODIFIED ALKALINE EARTH METAL CARBONATE-CONTAINING MATERIAL

CROSS-REFERENCE TO RELATED APPLICATIONS

This is a U.S. national phase of PCT Application No. PCT/EP2015/070162, filed Sep. 3, 2015, which claims priority to European Application No. 14184762.4, filed Sep. 15, 2014.

The present application relates to a dry process for preparing a surface-modified alkaline earth metal carbonate-containing mineral material as well as to products and uses thereof.

In many cases, alkaline earth metal carbonate-containing materials (e.g., calcium carbonate-containing materials) obtained in a dry process are desired to provide specific characteristics. On the one hand, if the materials are to be reintroduced into an aqueous environment (e.g. for the production of paints, coatings or for use as filler material in paper), it may be advantageous if said materials are rapidly wettable with water. On the other hand, if any lipophilic treatment is to be carried out, the surface of the mineral materials may be adapted in order support the wettability by lipophilic additives, such as fatty acids.

In the field of dry mineral processing, such as in dry grinding or surface treatment, many additives (e.g., glycols, lignin sulfonates or amines) are known to the skilled person. However, many of today's additives have several disadvantages. Some of these additives are very expensive while others have boiling points of below 250° C. and may be classified as volatile organic compounds (VOCs). One well-known dry grinding agent is monopropylene glycol (MPG). Other additives may also cause unwanted foaming in follow-up applications or may cause unwanted darkening of white minerals.

EP 2 377 900 refers to a process to modify at least part of the surface of at least one mineral material, and to the use of at least one agent as an additive in an aqueous suspension of mineral materials having a pH between 5 and 10, wherein the additive allows for the formation of a low volume high solids content filter or centrifuge cake by dewatering the suspension. Said at least one agent may be formed by mixing, in an aqueous environment, at least one phosphonic acid comprising compound with one or more metal cations or metal-comprising cationic compounds.

In general, organophosphonic acids, derivatives thereof (e.g., esters) and their corresponding salts are known as metal chelants which may also serve as scale inhibitors in aqueous systems by inhibiting the precipitation of calcium salts. For example, U.S. Pat. No. 4,802,990 discloses the use of 1-hydroxyethane 1,1-diphosphonic acid (HEDP) in combination with a second acid in an aqueous environment. According to US 2005/0096233, calcium carbonate and barium sulphate deposition in oil wells is inhibited by using a polymer featuring pendant phosphonate groups. U.S. Pat. No. 4,802,990 describes the use of organophosphonic acids to dissolve mineral salts. Likewise, their use as corrosion inhibitors and as fertilizer components is known from the prior art. Furthermore, organophosphonates may be used as mineral flotation agents (e.g., WO 02/089991). Certain phosphonates and also phosphonocarboxylic acids may influence the form of precipitated calcium carbonate when dosed during the precipitation process (see EP 1 151 966). Organophosphonic acids and derivatives thereof may further be employed in fluidizing systems as described, for example, in FR 2 393 037, DE 44 04 219, FR 2 393 037, and FR 2 765 495.

EP 2 194 103 relates to a process for manufacturing calcium carbonate-containing materials having a particle surface with improved adsorption properties for dispersants using at least one lithium ion-containing compound and the use of such calcium carbonate materials in paper, paints and plastics. The lithium ion-containing compound itself has no dispersing properties but may improve the adsorption of polyacrylate dispersant.

FR 7 816 616 refers to a mixture of pigments with 0.01 to 5 wt.-% of phosphonocarboxylic acid, or their salts, as dispersant in an aqueous environment to obtain a suspension having a solids content of from 30 to 80 wt.-%. According to one example, titanium dioxide is mixed with aluminium oxide and then ground and mixed with a number of additives, among which is 2-phosphonobutane-1,2,4-tricarboxylic acid (PBTC), to form a high solids content suspension that is stable over time.

However, the foregoing method used for the surface treatment of titanium dioxide generally requires the use of a strong acid in combination with an aluminium salt, such as sodium aluminate. Such a treatment is not suitable for acid sensitive materials such as alkaline earth metal carbonate-containing materials (e.g., calcium carbonate).

EP 2 029 677 refers to the use of, for example, polyethylene glycol homo- or copolymers as VOC-free dry grinding aids. However, these grinding aids are known to cause foaming in aqueous follow-up applications.

Moreover, many of the prior art processes relate to the modification of the surface characteristics of a mineral material being in the form of a suspension. As a major drawback, these suspensions require the use of suitable production plants and also processing plants, for example conveyor systems. In general, also costs for storage and transportation of liquids or suspensions are higher as compared to the costs for the corresponding dry materials.

In view of the foregoing, there is still a need for improved processes for the provision of alkaline earth metal carbonate-containing materials in order to overcome one or more of the foregoing drawbacks.

In this respect, one object of the present invention may be seen in the provision of an alkaline earth metal carbonate-containing material showing improved wetting properties.

Another object may be seen in the provision of an alkaline earth metal carbonate-containing material having improved wetting properties while simultaneously showing a reduced foaming tendency and/or a reduced VOC content.

Still another object of the present invention may be seen in the provision of a more efficient and more economic process for the preparation of alkaline earth metal carbonate-containing materials and, in particular, of such materials having improved wetting properties.

The foregoing and other problems may be solved by the subject-matter as defined herein in the independent claims.

A first aspect of the present invention relates to a process to modify at least part of the surface of an alkaline earth metal carbonate-containing material, the process comprising the following steps:
   (a) providing at least one alkaline earth metal carbonate-containing material;
   (b) providing at least one surface-modifying agent; and
   (c) dry blending the at least one alkaline earth metal carbonate-containing material provided in step (a) and the at least one surface-modifying agent provided in step (b) to obtain a blend;

wherein the at least one surface-modifying agent provided in step (b) comprises at least one of:
(i) an organophosphonic acid; and/or
(ii) derivatives of the organophosphonic acid;
wherein the organophosphonic acid and/or derivatives thereof may be partially or fully neutralized with at least one cation selected from mono-, di-, and trivalent cations; and
wherein said blend has a total moisture content of less than 2.0 wt.-%, based on the total weight of said blend.

The process according to the present invention is a dry process in which at least one alkaline earth metal carbonate-containing material and at least one surface-modifying agent are dry blended in order to modify at least part of the surface of the alkaline earth metal carbonate-containing material, wherein the resulting blend has a total moisture content of less than 2.0 wt.-%, based on the total weight of said blend. The surface-modifying agent comprises at least one of an organophosphonic acid and derivatives of the organophosphonic acid, both of which may be partially or fully neutralized with at least one cation selected from mono-, di-, and trivalent cations. It was found that these surface-modifying agents may readily react with the surface of the alkaline earth metal carbonate-containing material although no water or only minor amounts of water are present in the dry blend. Without being bound to any theory, it is believed that the agent employed in the present invention forms a deposit on the surface of the mineral material which proceeds via the formation of a chelate or salt complex.

Another aspect of the present invention relates to a mineral product. Said mineral product is obtainable by the inventive process.

Still another aspect of the present invention relates to the use of said mineral product in paper, plastics, sealants, paints, concretes and cosmetics, preferably in polyolefin products, more preferably in films and/or fibers, and most preferably in breathable films.

The following terms used throughout the present application shall have the meanings set forth below:

An "organophosphonic acid" in the meaning of the present invention may be any molecule comprising one or more phosphonic acid groups, —P(=O)(OH)$_2$, wherein these one or more groups are bound to said molecule by a covalent P—C bond. Accordingly, the simplest organophosphonic acid is methylphosphonic acid. In general, organophosphonic acids may be non-polymeric (i.e. monomeric), oligomeric or also polymeric. In case of oligomeric or polymeric phosphonic acids, the phosphonic acid groups may appear along polymer chains and may be introduced, for example, by polymerization of monomers comprising phosphonic acid groups (e.g., vinylphosphonic acid). In the meaning of the present application a "derivative" of an organophosphonic acid may thus be any molecule obtainable by a formal covalent replacement of a proton ("H") and/or hydroxy group ("OH") of a phosphonic acid group, —P(=O)(OH)$_2$, in any of the organophosphonic acids defined within this application. Typical derivates in the meaning of the present invention comprise phosphonic ester groups: —P(=O)(OH)(OR) or —P(=O)(OR)$_2$ or —P(=O)(OR)(OR').

The term "dry blending" in the meaning of the present application shall indicate that no dewatering or drying step is required during and/or after blending two or more components in order to achieve a defined total moisture content of the resulting blend, for example a total moisture content of less than 2.0 wt.-%, based on the total weight of said blend. Preferably, the term "dry blending" shall indicate that the at least one alkaline earth metal carbonate-containing material according to step (a) of the inventive process, the at least one surface-modifying agent according to step (b) of the inventive process and/or each further optional component used in a blending step have a total moisture content of less than 5.0 wt.-%, preferably less than 3.0 wt.-%, more preferably less than 2.0 wt.-%, and most preferably less than 1.0 wt.-%, each based on the total weight of the corresponding component.

The term "dry grinding" as used herein refers to a step of grinding a blend comprising solid material, wherein the total moisture content of said blend during grinding is less than 2.0 wt.-%, based on the total weight of the material.

Unless indicated otherwise, the "total moisture content" of a material refers to the percentage of moisture (i.e. water) which may be desorbed from a sample upon heating to 220° C. The total moisture contents as defined herein can be measured according to the Karl Fischer Coulometric titration method, desorbing the moisture in an oven at 220° C. for 10 min and passing it continuously into a KF Coulometer (Mettler-Toledo Coulometric KF Titrator C30, combined with Mettler-Toledo oven DO 0337) using dry nitrogen at 100 ml/min for 10 min. A calibration curve using water has to be recorded and a blank of 10 min nitrogen flow without a sample has to be taken into account.

Throughout the present application, the particle size of a fraction of a particulate material is described by its particle size distribution. The value $d_x$ represents the diameter relative to which x % by weight of the particles have diameters of less than $d_x$. This means, for example, that the $d_{98}$ value (also referred to as the "topcut") is the particle size at which 98 wt.-% of all particles of a fraction are smaller than the indicated value. The $d_{50}$ value is thus the "weight median particle size" at which 50 wt.-% of all particles are smaller than the indicated particle size. Particle sizes being smaller than 45 μm can be determined based on measurements made by using a Sedigraph™ 5120 instrument of Micromeritics Instrument Corporation. The method and the instrument are known to the skilled person and are commonly used to determine the particle size of fillers and pigments. The measurements are carried out in an aqueous solution of 0.1 wt.-% $Na_4P_2O_7$. Samples are dispersed using a high speed stirrer and supersonics. In case of particle sizes being 45 μm or larger, fractional sieving according to the ISO 3310-1: 2000 standard is used to determine particle size distributions.

The terms "coarse" and "fine" as used herein describe the particle size of two fractions of a particulate material relative to each other and, thus, do not imply a specific particle size or size range. Unless indicated otherwise, both terms refer to the relative weight median particle sizes $d_{50}$. In this respect, the term "fine fraction" indicates that the weight median particle size $d_{50}$ of said fraction is smaller than the weight median particle size $d_{50}$ of the corresponding "coarse fraction".

Throughout the present document, the "specific surface area" (expressed in m$^2$/g) of a material is determined by the BET method with nitrogen as adsorbing gas and by use of a Gemini V instrument from Micromeritics. The method is well known to the skilled person (ISO 9277:1995). Samples are conditioned at 250° C. for a period of 30 min prior to measurement. The total surface area (in m$^2$) of said material can be obtained by multiplication of the specific surface area (in m$^2$/g) and the mass (in g) of the material.

If necessary, solids contents of a suspension or dispersion as given herein in wt.-% are determined using a Mettler-Toledo LP16 PM100 mass balance equipped with an LP16 IR dryer.

The pH value of a suspension or dispersion is measured using a SevenMulti pH meter from Mettler-Toledo at 25° C.

Unless indicated otherwise the Brookfield viscosity is measured after one minute of stirring at 20° C.±2° C. at 100 rpm by the use of a Brookfield viscometer type RVT equipped with disc spindle 3 of the Brookfield RV spindle series.

The term "volatile onset temperature" in the meaning of the present application refers to a temperature at which volatiles—including volatiles introduced as a result of the present process—begin to evolve, as observed on a thermogravimetric (TGA) curve plotting the mass of remaining sample (y-axis) as a function of temperature (x-axis). In the present application, thermogravimetric analysis (TGA) is performed using a Mettler Toledo TGA 851 based on a sample size of 200±50 mg and scanning temperatures of from 25° C. to 500° C. at a rate of 20° C./min under an air flow of 70 ml/min. The first derivative of the TGA curve is obtained and the inflection points thereon between 150° C. and 500° C. are identified. Among these inflection points having a tangential slope value of greater than 45° relative to a horizontal line, the one having the lowest associated temperature above 200° C. is identified. The temperature associated with this lowest inflection point of the first derivative curve is the volatile onset temperature.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, e.g. the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

Advantageous embodiments of the process according to the present invention are defined in the corresponding subclaims. It is to be understood that the embodiments disclosed hereinafter may be combined with each other.

According to one embodiment of the present invention, the inventive process further comprises at least one of the following steps:
(d) dry grinding the blend in at least one grinding unit during and/or after step (c);
(e) classifying the blend to obtain one or more coarse fractions, wherein the coarse fractions are optionally subjected to another dry grinding step and/or optionally subjected to another classifying step, and one or more fine fractions.

According to another embodiment of the present invention, the alkaline earth metal carbonate-containing material provided in step (a) is a calcium-carbonate-containing material, and preferably is selected from the group consisting of dolomite, dolomitic and magnesitic marble, limestone, chalk, and precipitated calcium carbonate.

In another embodiment of the present invention, the alkaline earth metal carbonate-containing material provided in step (a) comprises less than 0.1 wt.-%, based on the weight of dry mineral material, of a polycarboxylate-based dispersant.

In another embodiment of the present invention, the organophosphonic acid is a substituted or unsubstituted alkylene diphosphonic acid.

According to another embodiment of the present invention, the organophosphonic acid is selected from methylene diphosphonic acid (MDP), hydroxymethylene diphosphonic acid (HMDP), 1-hydroxyethane-1,1-diphosphonic acid (HEDP), hydroxycyclohexylmethylene diphosphonic acid (HCMDP), 1-hydroxy-3-aminopropane-1,1-diphosphonic acid (APD), amino-tris(methylenephosphonic acid) (ATMP), diethylenetriamine penta(methylenephosphonic acid) (DTPMP), and phosphonosuccinic acid (PSA).

According to another embodiment of the present invention, the mono-, di-, and trivalent cations are selected from:
(i) Li, Na, K, $NH_4^+$,
    preferably Li, Na, K; and
(ii) Mg, Ca, Mn, Co, Cu, Zn, Sr, Zr, Sn,
    preferably Mg, Ca, Sr; and
(iii) Al, Cr, Fe,
    preferably Al;
wherein the organophosphonic acid and/or derivatives thereof are preferably neutralized to a degree of from 10 to 90%, more preferably from 30 to 80%, and most preferably from 40 to 60%, based on the total number of acidic protons in the organophosphonic acid and/or derivatives thereof.

According to still another embodiment of the present invention, the total amount of the at least one surface-modifying agent used in step (c) ranges from 0.01 to 5.0 wt.-%, preferably from 0.03 to 1.0 wt-%, and more preferably from 0.05 to 0.7 wt.-%, based on the dry weight of the alkaline earth metal carbonate-containing material provided in step (a).

According to still another embodiment of the present invention, the blend has a total moisture content of less than 2.0 wt.-%, preferably less than 1.5 wt.-%, more preferably less than 1.0 wt.-%, even more preferably less than 0.5 wt.-%, and most preferably from 0.03 to 0.2 wt.-%, based on the total weight of said blend.

In another embodiment of the present invention, the process further comprises a step of reacting the alkaline earth metal carbonate-containing material with a hydrophobizing agent during and/or after step (c), step (d), and/or step (e).

In one embodiment of the present invention, the mineral product obtainable according to the inventive process has a total moisture content of less than 2.0 wt.-%, preferably less than 1.5 wt.-%, more preferably less than 1.0 wt.-%, even more preferably less than 0.5 wt.-%, and most preferably from 0.03 to 0.2 wt.-%, based on the total weight of said mineral product.

According to another embodiment of the present invention, the mineral product has a weight median particle size $d_{50}$ of from 0.2 to 45 µm, preferably from 0.5 to 15 µm, and more preferably from 0.7 to 2 µm.

According to still another embodiment of the present invention, the mineral product has a specific surface area of from 0.5 to 60 m$^2$/g, more preferably from 2 to 15 m$^2$/g, and most preferably from 3 to 10 m$^2$/g, as measured by the BET nitrogen method.

The inventors found that the mineral product obtainable by the process of the present invention may be easily wettable depending on the selection of the surface-modifying agent, for example by lipophilic additives, such as fatty acids having six or more carbon atoms in the chain to render the particles hydrophobic.

The inventors also found that the mineral product obtainable by the process of the present invention may be easily wettable as well depending on the selection of the surface-modifying agent, for example by hydrophilic additives such as water which allows forming high solids mineral suspensions. Thus, easy water wettability of a mineral product is associated with easy dispersibility of the solid particles in water even at high concentrations (e.g., >50 wt.-%) while low Brookfield viscosities may be achieved, e.g., below 1,000 mPa·s which is particularly suitable for paper and paint applications.

In the following, preferred embodiments of the inventive process will be discussed in more detail. It is to be understood that these details and embodiments also apply to a mineral product obtainable by the inventive process and to its use in any of the specified applications.

Step (a)—The Alkaline Earth Metal Carbonate-containing Material

In step (a) of the process according to the present invention, at least one alkaline earth metal carbonate-containing material is provided. In general, said material may be of natural or synthetic origin.

An "alkaline earth metal carbonate" in the meaning of the present invention is a carbonate which comprises at least one type of alkaline earth metal cation. These alkaline earth metals may be beryllium, magnesium, calcium, strontium, barium, or radium.

According to one embodiment of the present invention, said alkaline earth metal carbonate is selected from magnesium carbonate, calcium carbonate, and strontium carbonate. Preferably, said alkaline earth metal carbonate is selected from magnesium carbonate and calcium carbonate, and more preferably is calcium carbonate. Therefore, according to a preferred embodiment of the present invention, the at least one alkaline earth metal carbonate-containing material is a calcium carbonate-containing material.

According to another embodiment of the present invention, the at least one alkaline earth metal carbonate-containing material may be selected from ground natural calcium carbonate (GNCC) and precipitated calcium carbonate (PCC), and preferably is a ground natural calcium carbonate (GNCC).

A "ground natural calcium carbonate" (GNCC) in the meaning of the present invention is a calcium carbonate obtained from natural sources, such as marble, limestone and chalk which may be optionally processed in a beneficiation step, such as flotation, bleaching or magnetic separation.

A "precipitated calcium carbonate" (PCC) in the meaning of the present invention is a synthesized material, which may be generally obtained by precipitation following the reaction of carbon dioxide and lime in an aqueous environment or by precipitation of a calcium (e.g., $CaCl_2$) and carbonate source (e.g., $Na_2CO_3$) in water. PCC may be metastable vaterite, stable calcite or aragonite.

According to another embodiment of the present invention, the at least one alkaline earth metal carbonate-containing material provided in step (a) is selected from the group consisting of dolomite, dolomitic and magnesitic marble, limestone, chalk, and precipitated calcium carbonate.

According to still another embodiment of the present invention, the at least one alkaline earth metal carbonate-containing material provided in step (a) is selected from the group consisting of dolomite, dolomitic and magnesitic marble, limestone, and chalk.

In general, the at least one alkaline earth metal carbonate-containing material provided in step (a) may contain at least 60.0 wt.-%, preferably at least 80.0 wt.-%, more preferably at least 90.0 wt.-%, even more preferably at least 95.0 wt.-%, and most preferably from 98.5 to 99.9 wt.-% of alkaline earth metal carbonate, based on the total dry weight of said material. Said at least one alkaline earth metal carbonate-containing material preferably contains less than 0.1 wt.-%, based on the total of said material, of quartz.

Suitably, the at least one alkaline earth metal carbonate-containing material of step (a) is provided as a solid material being in particulate form. In this respect, the at least one alkaline earth metal carbonate-containing material provided in step (a) may have any particle size distribution allowing the material to be subjected to a dry blending step. Accordingly, the calcium carbonate-containing material may be provided as a comminuted material, for example, in crushed or ground form.

Therefore, according to one embodiment of the present invention, the at least one alkaline earth metal carbonate-containing material of step (a) may be provided in crushed form. For example, said material may be crushed by use of a hammer mill, gyratory crusher, jaw crusher, or a cone crusher.

Additionally or alternatively, the at least one alkaline earth metal carbonate-containing material of step (a) may be provided in ground form. For this purpose, a ball mill, pin mill or any other known grinding unit may be used. If the at least one alkaline earth metal carbonate-containing material is provided in ground form, said ground material may further be classified to obtain one or more coarse fractions and one or more fine fractions, wherein the one or more fine fractions may then be provided as the at least one alkaline earth metal carbonate-containing material in process step (a).

Accordingly, in one embodiment of the present invention, the at least one alkaline earth metal carbonate-containing material provided in step (a) may have a weight median particle size $d_{50}$ ranging from 1.0 to 1,000 μm, preferably from 1.5 to 500 μm, and more preferably from 2.5 to 100 μm.

According to another embodiment of the present invention, the at least one alkaline earth metal carbonate-containing material provided in step (a) has a weight median particle size $d_{50}$ ranging from 0.2 to 45 μm, preferably from 0.5 to 15 μm, and more preferably from 0.7 to 2 μm.

According to still another embodiment of the present invention, the at least one alkaline earth metal carbonate-containing material provided in step (a) has a weight median particle size $d_{50}$ ranging from 0.05 to 25 μm, preferably from 0.1 to 10 μm, more preferably from 0.2 to 5 μm, and most preferably from 0.5 to 2 μm.

In a further embodiment of the present invention, the at least one alkaline earth metal carbonate-containing material provided in step (a) has a specific surface area of from 0.5 to 60 m²/g, more preferably from 2 to 15 m²/g, and most preferably from 3 to 10 m²/g, as measured by the BET nitrogen method.

According to the inventive process, the alkaline earth metal-containing material provided in step (a) is dry blended with a surface-modifying agent provided in step (b), wherein the resulting blend has a defined total moisture content which should be less than 2.0 wt.-%, based on the total weight of said blend. As already defined hereinabove, the term "dry blending" in the meaning of the present invention shall indicate that no additional dewatering or drying step is necessary in order to achieve the defined total moisture content of said blend. Therefore, it may be advantageous if also the at least one alkaline earth metal carbonate-containing material provided in step (a) has a specific total moisture content, preferably being below 2.0 wt.-%, based on the total weight of said material.

According to one embodiment of the present invention, the at least one alkaline earth metal carbonate-containing material provided in step (a) has a total moisture content of less than 2.0 wt.-%, preferably less than 1.5 wt.-%, more preferably less than 1.0 wt.-%, even more preferably less than 0.5 wt.-%, and most preferably from 0.03 to 0.2 wt.-%, based on the total weight of said material.

In some embodiments of the present invention, the at least one alkaline earth metal carbonate-containing material provided in step (a) has a total moisture content of less than 2.0 wt.-%, preferably less than 1.5 wt.-%, more preferably less than 1.0 wt.-%, even more preferably less than 0.5 wt.-%, and most preferably from 0.03 to 0.2 wt.-%, based on the total weight of said material, wherein the weight median particle size $d_{50}$ of said material may range from 1.0 to 1'000 µm, preferably from 1.5 to 500 µm, and more preferably from 2.5 to 100 µm.

If necessary, the total moisture content of the at least one alkaline earth metal carbonate-containing material provided in step (a) can be adjusted to specific values (e.g., to those specified hereinabove) prior to subjecting same to dry blending step (c), for example by drying.

As one further advantage, it was found that in the process of the present invention it is possible to omit polycarboxylate-based dispersants which would be associated with an unwanted increase of the moisture pick up susceptibility of the primary product.

Therefore, in a further embodiment of the present invention, the alkaline earth metal carbonate-containing material provided in step (a) comprises less than 0.1 wt.-%, based on the weight of dry mineral material, of a polycarboxylate-based dispersant.

Step (b)—The Surface-modifying Agent

According to step (b) of the process according to the present invention, at least one surface-modifying agent is provided, wherein the at least one surface-modifying agent comprises at least one of:
  (i) an organophosphonic acid; and
  (ii) derivatives of the organophosphonic acid.

Accordingly, the at least one surface-modifying agent may comprise an organophosphonic acid, derivatives of the organophosphonic acid, or a mixture of both.

As already defined hereinabove, an organophosphonic acid in the meaning of the present invention may be any molecule comprising one or more phosphonic acid groups, $-P(=O)(OH)_2$, wherein these one or more groups are bound to said molecule by a covalent P—C bond.

In general, the organophosphonic acid may be non-polymeric, oligomeric, and/or polymeric, wherein non-polymeric (i.e. monomeric) organophosphonic acids may be preferred.

Independently from whether the organophosphonic acid is non-polymeric, oligomeric or polymeric, it may comprise one or more phosphonic acid groups and, thus, may be selected from organomonophosphonic acids, an organodiphosphonic acids and the like.

Therefore, according to one embodiment of the present invention, the organophosphonic acid is an organophosphonic acid comprising from 1 to 200 phosphonic acid groups, preferably from 1 to 100 phosphonic acid groups, and more preferably from 1 to 50 phosphonic acid groups.

According to another embodiment of the present invention, the organophosphonic acid is a monomeric organophosphonic acid comprising from 1 to 10 phosphonic acid groups, preferably from 1 to 5 phosphonic acid groups, more preferably 2 or 3 phosphonic acid groups, and most preferably is a monomeric organodiphosphonic acid. One example for a (monomeric) organophosphonic acid may be phosphonosuccinic acid (PSA).

In still another embodiment of the present invention, the organophosphonic acid is a substituted or unsubstituted alkylene diphosphonic acid. Non-limiting examples include methylene diphosphonic acid (MDP) and hydroxymethylene diphosphonic acid (HMDP). A particularly preferred alkylene diphosphonic acid is 1-hydroxyethane-1,1-diphosphonic acid (HEDP).

HEDP has four acidic protons which is reflected by its four different $pK_a$ values being 1.7, 2.47, 7.28, and 10.29 as measured by acid-base titration in 0.1 M potassium chloride.

The carbon atom of a P—C bond present in the organophosphonic acid of this invention is a carbon atom of an organic group ("organo"). The skilled person will thus appreciate that such an organic group may be any suitable organic group known in the art of organic chemistry. In particular, an organic group (e.g., an alkylene group) in the meaning of the present invention may be any substituted (e.g., hydroxymethylene) or any unsubstituted organic group (e.g., methylene). Common substituents which may be present in such organic groups include, without being limited to, saturated and unsaturated alkyls, hydroxy (—OH), carboxyl (—CO$_2$H), sulfonyl (—SO$_3$H), halogene (—F, —Cl, —Br, —I), and amines (—NR$_2$).

In some embodiments of the present invention, said organophosphonic acid may be a organotriphosphonic acid, such as amino-tris(methylenephosphonic acid) (ATMP), or acids comprising a higher number of phosphonic acid groups, such as diethylenetriamine penta(methylenephosphonic acid) (DTPMP).

In a further embodiment of the present invention, the organophosphonic acid is selected from methylene diphosphonic acid (MDP), hydroxymethylene diphosphonic acid (HMDP), 1-hydroxyethane-1,1-diphosphonic acid (HEDP), hydroxycyclohexylmethylene diphosphonic acid (HC-MDP), 1-hydroxy-3-aminopropane-1,1-diphosphonic acid (APD), amino-tris(methylenephosphonic acid) (ATMP), diethylenetriamine penta(methylenephosphonic acid) (DTPMP), and phosphonosuccinic acid (PSA).

In still another embodiment of the present invention, the organophosphonic acid is oligomeric or polymeric, preferably said organophosphonic acid is obtainable by polymerization of a monomer mixture comprising at least one polymerizable phosphonic acid monomer.

In some embodiments according to the present invention, said monomer mixture has a molar ratio of phosphonic acid monomers (P) to non-phosphonic acid monomers (M) ranging from 20:1 to 1:20, preferably from 10:1 to 1:5, and more preferably from 5:1 to 1:2.

In addition or as an alternative to the organophosphonic acid, the at least one surface-modifying agent provided in step (b) may comprise derivatives of the organophosphonic acid. In this respect, a derivative may be any molecule obtainable by a formal covalent replacement of a proton ("H") and/or hydroxy group ("—OH") of a phosphonic acid group, $-P(=O)(OH)_2$, in an organophosphonic acid. Accordingly, a derivative in the meaning of the present invention may feature both single and double modifications of a phosphonic acid group (e.g., phosphonic acid esters include phosphonic acid monoesters or diesters). Moreover, in cases where an organophosphonic acid comprises two or more phosphonic acid groups (e.g., in case of an alkylene diphosphonic acid), its derivative may feature one or more such modified groups.

In one embodiment according to the present invention, the derivatives of the organophosphonic acid comprise one or more esterified phosphonic acid groups. In a further embodiment, said esterified phosphonic acid groups may be selected from substituted and/or unsubstituted alkyl esters, preferably having from 1 to 8 alkyl carbon atoms. More preferably, said esterified phosphonic acid groups may be selected from substituted and/or unsubstituted methyl esters, ethyl esters, propyl esters, and mixtures thereof.

The organophosphonic acid and/or derivatives of the organophosphonic acid may be partially or fully neutralized with at least one cation selected from mono-, di-, and trivalent cations.

The term "neutralized" in the meaning of the present invention shall indicate that acidic protons present in a molecule are replaced by other cations. In particular, acidic protons ("$H^+$") are those found in the following groups: $-P(=O)(OH)_2$, $-CO_2H$, and $-SO_3H$. Typically, neutralization may be accomplished by contacting an organophosphonic acid or derivatives of the organophosphonic acid with a base, such as an alkaline metal hydroxide (e.g., NaOH).

In one embodiment of the present invention, the at least one cation is selected from mono-, di-, and trivalent cations, preferably from mono- and divalent cations, and most preferably is a monovalent cation. A cation in the meaning of the present invention may be any positively charged ion and thus may include metal ions as well as non-metal cations, such as ammonium, iminium, and the like.

In another embodiment according to the present invention, the mono-, di-, and trivalent cations are selected from:
(i) Li, Na, K, $NH_4^+$,
preferably Li, Na, K; and
(ii) Mg, Ca, Mn, Co, Cu, Zn, Sr, Zr, Sn,
preferably Mg, Ca, Sr; and
(iii) Al, Cr, Fe,
preferably Al.

In still another embodiment according to the present invention, the mono-, di-, and trivalent cations are selected from:
(i) Li, Na, K; and
(ii) Mg, Ca, Sr; and
(iii) Al.

In still another embodiment of the present invention, the at least one cation is a metal cation, preferably selected from the group consisting of: Li, Na, K, and Ca.

The at least one surface-modifying agent of step (b) may be provided in undiluted form or in form of an aqueous solution. However, an aqueous solution may be preferred to ensure equal distribution of the agent in blending step (c). Said solution may be obtainable by mixing the at least one surface-modifying agent and water (e.g., tap water or deionized water).

Therefore, in embodiment of the present invention, the at least one surface-modifying agent of step (b) is provided in form of an aqueous solution, preferably the total content of agent in said solution ranges from 5.0 to 50.0 wt.-%, more preferably from 10.0 to 45.0 wt.-%, and most preferably from 20.0 to 40.0 wt.-%, based on the total weight of the solution.

In another embodiment of the present invention, the agent provided in step (b) is prepared by mixing water, at least one organophosphonic acid and at least one cation selected from mono-, di-, and trivalent cations, preferably selected from Li, Na, K, Mg, Ca, Sr, and Al.

As already indicated above, the organophosphonic acid or derivatives of the organophosphonic acid may be partially or fully neutralized meaning that part ("partially") or all ("fully") of the acidic protons present in the organophosphonic acid or the corresponding derivatives are replaced by other cations. The degree of neutralization may be based on the total number of acidic protons in the organophosphonic acid or the corresponding derivatives. For example, a neutralization degree of 100% indicates that any acidic proton present in the organophosphonic acid or the corresponding derivatives is replaced by another cation.

In some embodiments according to the present invention, the organophosphonic acid and/or derivatives thereof are neutralized to a degree of from 10 to 90%, more preferably from 30 to 80%, and most preferably from 40 to 60%, based on the total number of acidic protons in the organophosphonic acid and/or derivatives thereof In an another embodiment of the present invention, the at least one agent provided in step (b) is prepared by mixing submolar quantities of sodium, lithium and/or calcium cations, preferably provided in the form of hydroxides or carbonates, with HEDP. Therefore, in one embodiment of the present invention, the at least one surface-modifying agent comprises at least one of $Na_2HEDP$, $Li_2HEDP$, $Na_3HEDP$, NaCaHEDP, $Na_4HEDP$, and $Li_2CaHEDP$.

In still another embodiment of the present invention, said at least one surface-modifying agent is prepared by mixing a sodium ion source and/or HEDP sodium salt with HEDP, preferably in a weight ratio of from 1:1 to 50:1, more preferably from 7:3 to 25:1, and most preferably 9:1 to 2:1.

Examples for suitable sodium ion sources include, without being limited to, sodium hydroxide, sodium carbonate, and sodium hydrogen carbonate.

In cases where the at least one surface-modifying agent is provided as an aqueous solution, said solution may have a pH of from 1 to 13, and preferably from 4 to 10.

Steps (c) to (e)—Dry Blending, Dry Grinding, Classifying

In step (c) of the process according to the present invention, the at least one alkaline earth metal carbonate-containing material provided in step (a) and the at least one surface-modifying agent provided in step (b) are dry blended, meaning that no dewatering or drying step is required during and/or after blending in order to achieve the defined total moisture content of the resulting blend, for example a total moisture content of less than 2.0 wt.-%, based on the total weight if said blend. The skilled person will recognize that it is possible to produce blends having a low total moisture content (e.g., less than 2.0 wt.-%) even in cases where the at least one surface-modifying agent is provided in form of an aqueous solution.

The total amount of said at least one surface-modifying agent used in step (c) may range from 0.01 to 5.0 wt.-%, preferably from 0.03 to 1.0 wt-%, and more preferably from 0.05 to 0.7 wt.-%, based on the dry weight of the alkaline earth metal carbonate-containing material provided in step (a).

In a further embodiment according to the present invention, the total amount of the at least one surface-modifying agent used in step (c) may range from 0.01 to 5.0 wt.-%, preferably from 0.03 to 1.0 wt-%, and more preferably from 0.05 to 0.7 wt.-%, based on the dry weight of the alkaline earth metal carbonate-containing material provided in step (a), wherein said at least one surface-modifying agent is provided in form of an aqueous solution, wherein the total content of agent in said solution preferably ranges from 5.0 to 50.0 wt.-%, more preferably from 10.0 to 45.0 wt.-%, and most preferably from 20.0 to 40.0 wt.-%, based on the total weight of the solution.

The skilled person will appreciate that the at least one alkaline earth metal carbonate-containing material provided in step (a) may undergo reactions with the at least one surface-modifying agent provided in step (b) as a consequence of dry blending step (c). Typically, these reactions include neutralization reactions, wherein one or more acidic protons present in the at least one surface-modifying agent may be replaced by other cations present in the blend (e.g., calcium ions). In cases where the surface-modifying agent is provided in partially or fully neutralized form, the at least one cation of said partially or fully neutralized form may be replaced by any other cation present in the blend.

Accordingly, in one embodiment, the at least one surface-modifying agent provided in step (b) is partially or fully neutralized after step (c) by alkaline earth metal ions and preferably by calcium ions.

In still another embodiment of the present invention, the process further comprises at least one and preferably both of the following steps:
  (d) dry grinding the blend in at least one grinding unit during and/or after step (c);
  (e) classifying the blend to obtain one or more coarse fractions, wherein the coarse fractions are optionally subjected to another dry grinding step and/or optionally subjected to another classifying step, and one or more fine fractions.

Depending on the particle size distribution (e.g., $d_{50}$) of the alkaline earth metal carbonate-containing material subjected to dry blending step (c), a grinding step by use of at least one grinding unit may be advantageous in order to achieve the desired particle size distribution of the final product.

For the purposes of the present invention, any suitable grinding unit known in the art may be used, for example a ball mill, or a pin mill. However, said at least one grinding unit preferably comprises a ball mill.

It has to be noted that grinding step (d) is carried out by use of at least one grinding unit, i.e. it is possible to grind the alkaline earth metal carbonate-containing material in one or more grinding units. Therefore, it is also possible to use a series or cascade of grinding units which may be selected, for example, from any of the aforementioned mill types.

Dry grinding step (d) may be carried out in at least one grinding unit during and/or after dry blending step (c) and preferably is carried out during dry blending step (c).

Dry blending step (c) may be carried out in any of the at least one grinding units if a series or cascade of grinding units is used for this purpose. For example, if a series or cascade of two grinding units is used, it is possible to dry blend the at least one alkaline earth metal carbonate-containing material provided in step (a) and the at least one surface-modifying agent provided in step (b) during grinding in a first grinding unit to obtain a blend and, thereafter, subjecting the blend to a second grinding unit.

Additionally or alternatively to dry grinding step (d), the process according to the present invention may further comprise process step (e) according to which the blend is classified to obtain one or more coarse fractions, wherein the coarse fractions are optionally subjected to another dry grinding step and/or optionally subjected to another classifying step, and one or more fine fractions. For example, if the at least one alkaline earth metal carbonate-containing material of step (a) is already provided in ground form, the process may further comprise a classifying step (e) but no grinding step (d).

A classifying step in general serves to divide a feed fraction having a certain particle size distribution into a coarse fraction and a fine fraction each having different particle size distributions. Typically, the coarse fraction has a $d_{50}$ value being higher than that of the feed fraction, whereas the fine fraction has a $d_{50}$ value being smaller than the $d_{50}$ value of the feed fraction. Therefore, in one embodiment of the present invention, the one or more fine fractions have a weight median particle size $d_{50}$ ranging from 0.2 to 45 μm, preferably from 0.5 to 15 μm, and more preferably from 0.7 to 2 μm.

For the purpose of classifying, screening devices as well as gravity-based devices, such as centrifuges or cyclones, and any combination of the aforementioned devices may be used. In this respect, it has to be noted that it is also possible to use a series or cascade of any of the aforementioned classifying devices in any combination.

In one embodiment of the present invention, classifying step (e) is carried out by use of one or more cyclones. Optionally, said one or more cyclones are used in combination with one or more screens.

In a further embodiment of the present invention, the one or more coarse fractions are subjected to another dry grinding step and preferably to dry grinding step (d). In the latter case, the inventive process can be considered as a closed circuit grinding.

Independently from whether the inventive process comprises steps (a) to (c) only, or further comprises one or both of steps (d) and (e), said process may be carried out either as batch or continuous process. Preferably, the process according to the present invention is a continuous process.

Accordingly, in a preferred embodiment of the present invention, the inventive process is a continuous process further comprising the following steps:
  (d) dry grinding the blend in at least one grinding unit during step (c); and
  (e) classifying the blend to obtain one or more coarse fractions, wherein the coarse fractions are subjected to dry grinding step (d), and one or more fine fractions.

As already described hereinabove, the total amount of the at least one surface-modifying agent used in step (c) is based on the dry weight of the alkaline earth metal carbonate-containing material provided in step (a). In a continuous process, the amount of the alkaline earth metal carbonate-containing material provided in step (a) may preferably be adapted such that it corresponds to the amount which is removed from the process as a final product, for example as the blend obtained after step (c), as the blend extracted from an outlet of the one or more grinding units used in step (d), or as the one or more fine fractions obtained in process step (e).

In a further embodiment of the present invention, the process comprises a step of reacting the alkaline earth metal carbonate-containing material with a hydrophobizing agent during and/or after step (c), step (d), and/or step (e). Preferably, said hydrophobizing agent may be selected from fatty acids, monosubstituted succinic anhydrides, monosubstituted succinic acids, silanes, siloxanes, phosphates, phosphonates, oxalates, fluorides, and mixtures thereof. More preferably, the hydrophobizing agent is selected from the group consisting of fatty acids having from 6 to 24 carbons in the chain, phosphate esters, succinic acid anhydrides, and mixtures thereof The blend obtained by the inventive process may comprise further additives known in the art, for example a grinding agent. Accordingly, in one embodiment of the present invention, the blend further comprises at least one additive selected from glycols, preferably said additive is selected from ethylene glycol, diethylene glycol, triethylene glycol, monopropylene glycol, polyethylene glycols, polypropylene glycols, and polyethylene-propylene glycols.

The Mineral Product

The mineral product obtainable by the inventive process may be any product obtainable after carrying out process steps (a) to (c) and, optionally, any of the further process steps described hereinabove.

In one embodiment of the present invention, the mineral product obtainable by the inventive process may have a weight median particle size $d_{50}$ ranging from 1.0 to 1,000 µm, preferably from 1.5 to 500 µm, and more preferably from 2.5 to 100 µm.

According to another embodiment of the present invention, the mineral product obtainable by the inventive process has a weight median particle size $d_{50}$ ranging from 0.2 to 45 µm, preferably from 0.5 to 15 µm, and more preferably from 0.7 to 2 µm.

According to still another embodiment of the present invention, the mineral product obtainable by the inventive process has a weight median particle size $d_{50}$ ranging from 0.05 to 25 µm, preferably from 0.1 to 10 µm, more preferably from 0.2 to 5 µm, and most preferably from 0.5 to 2 µm.

Additionally or alternatively to the weight median particle size $d_{50}$, the mineral product obtainable by the inventive process may have a particle size topcut $d_{98}$ ranging from 1.0 to 10,000 µm, preferably from 1.5 to 1,000 µm, and more preferably from 2.5 to 50 µm.

According to another embodiment of the present invention, the mineral product obtainable by the inventive process may have a particle size topcut $d_{98}$ ranging from 0.5 to 30.0 µm, preferably from 1.0 to 20.0 µm, and more preferably from 1.5 to 15.0 µm.

The mineral product of the present invention is obtained in a dry process comprising a dry blending step and optional dry grinding and classification steps. Accordingly, the mineral product may be a dry solid material having a total moisture content of less than 2.0 wt.-%, preferably less than 1.5 wt.-%, more preferably less than 1.0 wt.-%, even more preferably less than 0.5 wt.-%, and most preferably from 0.03 to 0.2 wt.-%, based on the total weight of said mineral product.

In a further embodiment of the present invention, the mineral product obtainable by the inventive process has a specific surface area of from 0.5 to 60 m²/g, more preferably from 2 to 15 m²/g, and most preferably from 3 to 10 m²/g, as measured by the BET nitrogen method.

The mineral product obtainable by the inventive process may be used in a number of applications. In particular, said mineral product may be used in paper, plastics, sealants, paints, concretes and cosmetics, preferably in polyolefin products, more preferably in films and/or fibers, and most preferably in breathable films.

The skilled man will recognize that the dry product provides the general advantage of not being based on oil-based products. Moreover, the mineral product obtainable by the inventive process does not lead to the emission of volatiles upon incorporation into polymer articles at typical processing temperatures, even above 350° C., for example above 500° C.

Therefore, in one embodiment of the present invention, the mineral product has a volatile onset temperature of at least 350° C., preferably at least 450° C., and more preferably at least 500° C.

Due to the foregoing observation, the skilled person will also recognize that the dry product does not require any VOC declaration which may be of great value, for example if used in interior and exterior water based paints.

Unlike the mineral product of the present invention, conventional wet carbonate suspensions need to be stabilized with biocides whereas the inventive mineral products are far less sensitive towards bacterial contamination.

In general, the mineral product obtainable according to the inventive process has no limited shelf life and does not require periodical quality checks. Therefore, the inventive mineral products can be stored for a long period without any loss of quality. Mineral products obtained in a dry process offer much more flexibility to the customer due to the fact that no additional water is introduced with said mineral product into a given formulation.

The mineral product of the present invention may also be used in solvent based paint formulations. Water based suspension would not be suitable for these solvent based paint formulations. The same applies to sealant applications.

In some applications (e.g., in paper products, paints, coatings), the mineral products may be used in the form of aqueous suspensions. Such aqueous suspensions may be easily prepared—even at high solids content—from the mineral products according to the present invention. The inventive mineral products show good wetting properties allowing for a rapid dispersion of the solid material upon stirring. The solids content of these suspensions may range from 10 to 85 wt.-% and preferably from 50 to 80 wt.-%, based on the weight of said suspension.

The pH value of aqueous suspensions prepared from the mineral product of the present invention may be in the range of from 7.5 to 10.5.

In other applications the mineral product obtainable by the inventive process may be used directly, for example as filler in polymer articles.

EXAMPLES

The scope and interest of the invention may be better understood on basis of the following examples which are intended to illustrate embodiments of the present invention. However, they are not to be construed to limit the scope of the claims in any manner whatsoever.

Materials

Agent 1

Monopropylene glycol (MPG), CAS 57-55-6, purchased from Fluka, pH of 20 wt.-% solution in water: 8.2.

Agent 2

Tetrasodium 1-hydroxyethane-1,1-diphosphonate (Na$_4$HEDP), CAS 29329-71-3, purchased as Dequest 2016 from Italmatch Chemicals, 35.5 wt.-% in water, pH of 20 wt.-% solution in water: 11.76.

Agent 3

1-Hydroxyethane-1,1-diphosphonic acid (HEDP), CAS 2809-21-4, purchased as Dequest 2010 from Italmatch Chemicals, also referred to as "etidronic acid", 31.1 wt.-% in water, pH of 1 wt.-% solution in water: <2.0.

Agent 4

Dilithium 1-hydroxyethane-1,1-diphosphonate (Li$_2$HEDP). This agent is prepared by dissolving 36.8 g (0.1 mol) HEDP in 183.8 ml water. Thereafter, 8.39 g (0.2 mol) Li(OH).H$_2$O are added to the solution in four portions under stirring for 2 h to form Li$_2$HEDP. The reaction is slightly exothermic (33° C.) and a slight turbidity occurs. After 24 h, the formation of a gel is observed, the pH is 2.9, the solids content is 11.7 wt.-%. The gel is still stable after 96 h.

Raw material 1: Marble
Italian marble of the Pisa region, median stone size 5 to 50 cm, purity 99.5 wt.-% calcium carbonate (EDTA titration), HCl insolubles 0.5 wt.-% (mainly silicates and traces of pyrite).

Example 1

Pilot Scale

This example illustrates steps (a) to (e) of the inventive process and includes dry grinding in a ball mill in combination with a step of selection by a classifier. Raw material 1, before grinding in the ball mill, is crushed in a hammer mill. The size distribution of raw material 1 is shown in Table 1.

TABLE 1

Particle size distribution of raw material 1.

| Particle diameter | wt.-% |
| --- | --- |
| 1 mm-5 mm | 17.0 |
| 500 μm-1 mm | 16.5 |
| 200-500 μm | 18.8 |
| 100-200 μm | 12.8 |
| 45-100 μm | 16.3 |
| <45 μm | 18.4 |
| d$_{50}$ | ≈220 μm |
| Moisture content | 0.15 wt.-% |

Raw material 1 (see Table 1) is fed into a ball mill (Hosokawa™ Ball Mill S.O. 80/32) using 100 kg of iron grinding beads of the type Cylpeb™ in barrel form at a median diameter of 25 mm. Grinding was performed in a continuous mode.

The outlet of the grinding chamber at a size of 20×6 mm$^2$ is connected to an Alpine Turboplex™ 100 ATP classifier. At an air flow of 150 m$^3$/h, the speed of the classifier is adjusted such that a fine fraction of the desired fineness is produced. The fine fraction is removed. The coarse fraction is fed back into the inlet of the grinding chamber. The quantity of extracted fine fraction is replaced by fresh feed material at the inlet of the grinding chamber so that a total amount of 15 kg mineral is constantly in the system. The system is run for at least 2 h to stabilize the process before the fine fractions are removed for use in further steps.

In Trials A-C, different agents are added continuously into the inlet of the grinding chamber and dosed relative to the amount of fine fractions extracted from the classifier. The temperature of the mineral material in the grinder after 2 h is constantly between 80 and 82° C. until to the end of each trial after 6 h.

TABLE 2

| Trial | Agent No. | Amount [ppm] | Classifier speed [rpm] | d$_{98}$<br>wt.-% <2 μm<br>wt.-% <1 μm<br>wt.-% <0.5 μm<br>wt.-% moisture | Capacity [kg/h] |
| --- | --- | --- | --- | --- | --- |
| A | 1 | 1500 | 10'000 | 4.3<br>80.0<br>47.6<br>18.2<br>0.14 | 1.8 |
| B | 2 | 1500 | 10'000 | 3.9<br>82.4<br>50.6<br>21.0<br>0.25 | 1.5 |
| C | 2 + 3 | 1350 + 150 | 10'000 | 3.5<br>85.4<br>53.7<br>24.9<br>0.19 | 1.5 |

The results in Table 2 show equal capacity at equal fineness in case of phosphonic acid agents (Trials B+C) when compared with MPG (Trial A).

Example 2

Suitability for Plastic Applications

TABLE 3

Volatile onset temperatures of Trials A-C

| Trial | Agent No. | Volatile onset temperature [° C.] |
| --- | --- | --- |
| A | 1 | 188 |
| B | 2 | >500 |
| C | 3 | >500 |

Example 3

Suitability of Suspension for Paper Applications

TABLE 4

Suspension viscosity at high solids content.

| Trial | Agent No. | Solids content [wt.-%] | Brookfield viscosity [mPa · s] | pH of suspension |
| --- | --- | --- | --- | --- |
| A | 1 | 51.8 | 2048 | 8.01 |
| B | 2 | 68.3 | 366 | 10.03 |
| C | 3 | 75.6 | 448 | 9.46 |

Brookfield viscosities (spindle 3) of the corresponding samples are measured 1 h after preparation. The viscosities of the inventive products are far below 1'000 mPa.s which is necessary for easy pumping and also above 100 mPa.s which prevents unwanted sedimentation.

Example 4

Filler Slurry for Paint and Paper Applications

This example illustrates the use of the product obtained by steps (a) to (c) of the invention. 200 g water and 300 g of a mineral product obtained as described for Trial B of Example 1are mixed in order to obtain a mixture of the mineral product. The mineral product has a final particle size distribution of 62 wt.-%<2 µm, 34 wt.-%<1 µm and a $d_{50}$ of 1.7 µm. The resulting mixture is stirred for 20 min at 30° .C. The pH value of the obtained suspension is 8.4 and the Brookfield viscosity is 696 mPa.s(spindle 3).

The suspension is stirred for a further 30 min at 30° .C. The pH value now is 8.9 and the Brookfield viscosity is 582 mPa.s(spindle 3). The suspension is stored for 96 h at 23° .C and then is stirred for 5 min. The pH value now is 8.7.

The invention claimed is:

1. A process to modify at least part of a surface of an alkaline earth metal carbonate-containing material, the process comprising the following steps:
    (a) providing at least one alkaline earth metal carbonate-containing material;
    (b) providing at least one surface-modifying agent; and
    (c) dry blending the at least one alkaline earth metal carbonate-containing material provided in step (a) and the at least one surface-modifying agent provided in step (b) to obtain a blend;
    (d) dry grinding the blend in at least one grinding unit during and/or after step (c);
    (e) classifying the blend to obtain one or more coarse fractions, wherein the coarse fractions are optionally subjected to another dry grinding step and/or optionally subjected to another classifying step, and one or more fine fractions;
    wherein the at least one surface-modifying agent provided in step (b) comprises at least one of:
    (i) an organophosphonic acid; and
    (ii) derivatives of the organophosphonic acid;
    wherein the organophosphonic acid and/or derivatives thereof are optionally partially or fully neutralized with at least one cation comprising mono-, di-, or trivalent cations; and
    wherein the blend has a total moisture content of less than 2.0 wt.-%, based on the total weight of the blend.

2. The process of claim 1, wherein the alkaline earth metal carbonate-containing material provided in step (a) is a calcium-carbonate-containing material.

3. The process of claim 1, wherein the alkaline earth metal carbonate-containing material provided in step (a) comprises less than 0.1 wt.-%, based on the weight of dry mineral material, of a polycarboxylate-based dispersant.

4. The process of claim 1, wherein the organophosphonic acid is a substituted or unsubstituted alkylene diphosphonic acid.

5. The process of claim 1, wherein the organophosphonic acid comprises methylene diphosphonic acid (MDP), hydroxymethylene diphosphonic acid (FLVDP), 1-hydroxyethane-1, 1-diphosphonic acid (HEDP), hydroxycyclohexyltmethylene diphosphonic acid (HCMDP), 1-hydroxy-3-aminopropane-1, 1-diphosphonic acid (APD), amino-tris (methylene-phosphonic acid) (ATMP), diethylenetriamine penta(methylenephosphonic acid) (DTPMP), or phosphonosuccinic acid (PSA).

6. The process of claim 1, wherein the mono-, di-, and tri cations comprises:
    (i) Li, Na, K, or $NH_4^+$; and
    (ii) Mg, Ca, Mn, Co, Cu, Zn, Sr, Zr, or Sn; or
    (iii) Al, Cr, or Fe;
    wherein the organophosphonic acid and/or derivatives thereof are neutralized to a degree of from 10% to 90% based on the total number of acidic protons in the organophosphonic acid and/or derivatives thereof.

7. The process of claim 1, wherein the total amount of the at least one surface-modifying agent used in step (c) ranges from 0.01 wt.-% to 5.0 wt.-% based on the dry weight of the alkaline earth metal carbonate-containing material provided in step (a).

8. The process of claim 1, wherein the blend has a total moisture content of less than 1.0 wt,-%, based on the total weight of the blend.

9. The process of claim 1, wherein the process further comprises a step of reacting the alkaline earth metal carbonate-containing material with a hydrophobizing agent during and/or after step (c), step (d), and/or step (e).

10. The process of claim 2, wherein the calcium-carbonate containing material comprises dolomite, dolomitic and magnesitic marble, limestone, chalk, precipitated calcium carbonate, or mixtures thereof.

11. The process of claim 6, wherein the mono-, di-, and trivalent cations comprise:
    (i) Li, Na, or K; and
    (ii) Mg, Ca, or Sr; and
    (iii) Al.

12. The process of claim 6, wherein the mono-, di-, and trivalent cations comprise Li, Na, K, and Ca.

13. The process of claim 6, wherein the organophosphonic acid and/or derivatives thereof are neutralized to a degree of from 30% to 90%, based on the total number of acidic protons in the organophosphonic acid and/or derivatives thereof.

14. The process of claim 1, wherein the total amount of the at least one surface-modifying agent used in step (c) ranges from 0.03 wt.-% to 1.0 wt.-%, based on the dry weight of the alkaline earth metal carbonate-containing material provided in step (a).

15. The process of claim 1, wherein the blend has a total moisture content of less than 1.5 wt.-%, based on the total weight of the blend.

* * * * *

UNITED STATES PATENT AND TRADEMARK OFFICE
CERTIFICATE OF CORRECTION

PATENT NO. : 10,836,646 B2
APPLICATION NO. : 15/510771
DATED : November 17, 2020
INVENTOR(S) : Buri et al.

Page 1 of 1

It is certified that error appears in the above-identified patent and that said Letters Patent is hereby corrected as shown below:

In the Claims

Column 19, Line 49, Claim 5, delete "(FLVDP)," and insert --(HMDP),-- therefor

Column 19, Lines 50-51, Claim 5, delete "hydroxycyclohexyltmethylene" and insert --hydroxycyclohexylmethylene-- therefor Column 20, Line 5, Claim 6, delete "tri" and insert --trivalent-- therefor Column 20, Line 20, Claim 8, delete "wt,-%," and insert --wt.-%,-- therefor Signed and Sealed this
Sixteenth Day of March, 2021

Drew Hirshfeld
*Performing the Functions and Duties of the
Under Secretary of Commerce for Intellectual Property and
Director of the United States Patent and Trademark Office*